United States Patent
Hsu et al.

(10) Patent No.: US 11,090,023 B2
(45) Date of Patent: *Aug. 17, 2021

(54) NETWORK-CONNECTED ELECTRONIC STETHOSCOPE SYSTEMS

(71) Applicant: Heroic Faith Medical Science Co., Ltd., Grand Cayman (KY)

(72) Inventors: Fushun Hsu, Taipei (TW); Fu Ji Tsai, Taipei (TW); Yuan Ren Cheng, Taipei (TW)

(73) Assignee: Heroic Faith Medical Science Co., Ltd., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 16/786,728

(22) Filed: Feb. 10, 2020

(65) Prior Publication Data
US 2020/0178924 A1    Jun. 11, 2020

Related U.S. Application Data

(63) Continuation of application No. 16/366,845, filed on Mar. 27, 2019, now Pat. No. 10,555,717, which is a
(Continued)

(51) Int. Cl.
*A61B 7/04* (2006.01)
*A61B 7/02* (2006.01)
(Continued)

(52) U.S. Cl.
CPC .............. *A61B 7/04* (2013.01); *A61B 5/0004* (2013.01); *A61B 5/6843* (2013.01); *A61B 7/02* (2013.01);
(Continued)

(58) Field of Classification Search
CPC ....... A61B 7/04; A61B 5/0004; A61B 5/6843; A61B 7/02; A61B 2560/0247; A61B 2562/0204; H04L 67/12
See application file for complete search history.

(56) References Cited

U.S. PATENT DOCUMENTS 5,467,775 A   11/1995   Callahan et al.
5,616,845 A    4/1997   Hickling et al.
(Continued)

FOREIGN PATENT DOCUMENTS

WO    2017141165 A1    8/2017

OTHER PUBLICATIONS

International Search Report and Written Opinion of PCT Application No. PCT/US2018/053397, filed Sep. 28, 2018, dated Dec. 12, 2018, 11 pages.
(Continued)

*Primary Examiner* — Andrew L Sniezek
(74) *Attorney, Agent, or Firm* — Perkins Coie LLP; Andrew T. Pettit; Viola T. Kung

(57) ABSTRACT

Introduced here are electronic stethoscope systems designed to simultaneously monitor sounds originating from within a body under examination and the ambient environment. An electronic stethoscope system can include one or more input units that are connected to a hub unit. Each input unit may have at least one auscultation microphone and at least one ambient microphone. To improve the quality of sound recorded by an input unit, a processor can apply a noise cancellation algorithm that considers as input the audio data produced by the auscultation microphone(s) and the audio data produced by the ambient microphone(s). The audio data may be digitized directly in the input unit, and then transmitted to the hub unit for synchronization. For example, by examining the audio data produced by the ambient microphone(s), the processor may discover which digital artifacts, if any, should be filtered from the audio data produced by the auscultation microphone(s). The processor may reside within the input unit or the hub unit.

18 Claims, 13 Drawing Sheets

Related U.S. Application Data continuation of application No. PCT/US2018/053397, filed on Sep. 28, 2018.

(60) Provisional application No. 62/564,276, filed on Sep. 28, 2017.

(51) Int. Cl.
    *A61B 5/00*         (2006.01)
    *H04L 29/08*      (2006.01)

(52) U.S. Cl.
    CPC ............ *A61B 2560/0247* (2013.01); *A61B 2562/0204* (2013.01); *H04L 67/12* (2013.01)

(56) References Cited

U.S. PATENT DOCUMENTS

| | | | | |
|---|---|---|---|---|
| 10,555,717 B2 * | 2/2020 | Hsu | ............ | A61B 5/6843 |
| 2001/0014162 A1 * | 8/2001 | Orten | ............ | A61B 7/04 |
| | | | | 381/67 |
| 2004/0032957 A1 | 2/2004 | Mansy et al. | | |
| 2006/0227979 A1 | 10/2006 | Chen | | |
| 2008/0154144 A1 | 6/2008 | Unver et al. | | |
| 2009/0232322 A1 | 9/2009 | Tseng et al. | | |
| 2011/0222373 A1 | 9/2011 | Lee | | |
| 2012/0306677 A1 | 12/2012 | Medina et al. | | |
| 2014/0371631 A1 | 12/2014 | Fontana | | |
| 2015/0119758 A1 | 4/2015 | Rogers et al. | | |
| 2016/0045183 A1 | 2/2016 | Lee et al. | | |
| 2017/0251997 A1 | 9/2017 | Chung et al. | | |
| 2017/0265781 A1 | 9/2017 | Larson et al. | | |
| 2018/0177484 A1 | 6/2018 | Habboushe et al. | | |
| 2019/0142686 A1 * | 5/2019 | Lee | ............ | A61H 1/00 |
| | | | | 601/44 |
| 2019/0298296 A1 * | 10/2019 | Boatsman | ............ | A61B 7/00 |

OTHER PUBLICATIONS

EPO, Extended European Search Report for European Patent Application No. 18861470.5. dated May 19, 2021. 4 pages.

* cited by examiner

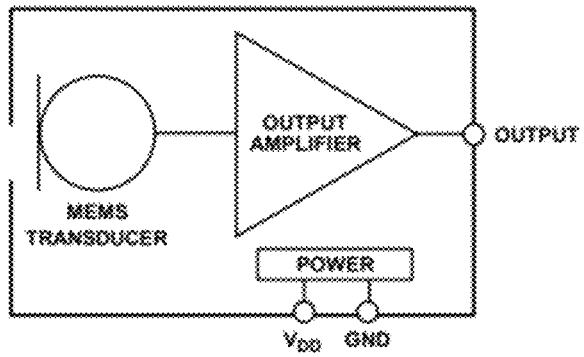
Example 1. Block diagram of typical analog MEMS microphone.
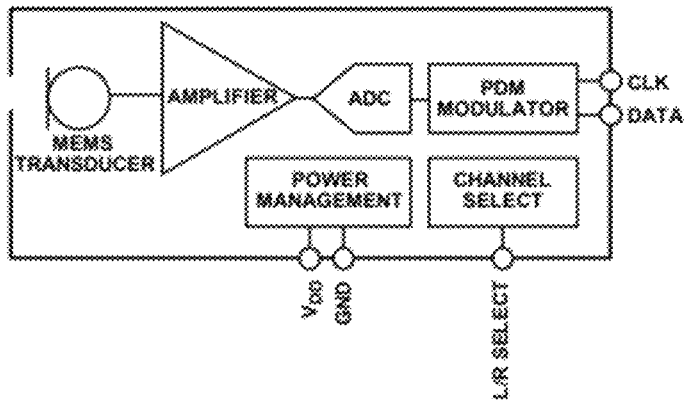
Example 2. Block diagram of typical PDM MEMS microphone.
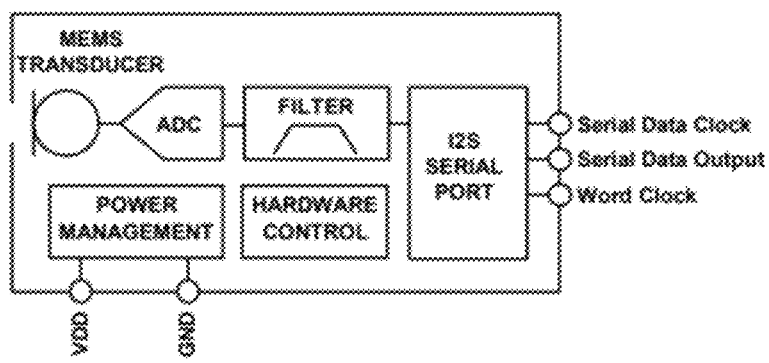
Example 3. Block diagram of typical I²S MEMS microphone.
FIGURE 10

1100

1101

Determine input unit(s) have been properly secured to the surface of a body under examination

1102

Generate audio data by initiating recording by microphone(s)

1103

Transmit the audio data to a hub unit for further review

1104

Discover or monitor a biometric characteristic by examining the audio data

1105

Cause display of information related to the biometric characteristic

1106

Transmit at least some of the audio data to another computing device across a network

FIGURE 11

NETWORK-CONNECTED ELECTRONIC STETHOSCOPE SYSTEMS

CROSS REFERENCE TO RELATED APPLICATIONS

This application is a continuation of U.S. patent application Ser. No. 16/366,845, filed Mar. 27, 2019; which is a continuation of PCT Application No. PCT/US2018/053397, filed on Sep. 28, 2018; which claims priority to U.S. Provisional Patent Application No. 62/564,276, filed Sep. 28, 2017; which are incorporated herein by reference in their entireties.

TECHNICAL FIELD

Various embodiments pertain to electronic stethoscope systems designed to simultaneously monitor sounds originating from within a body under examination and the ambient environment.

BACKGROUND

Conventionally, acoustic stethoscopes have been used for auscultation (i.e., listening to internal sounds originating from within a body). Acoustic stethoscopes often include a single chestpiece having a resonator designed to be placed against the body and a pair of hollow, air-filled tubes that are connected to earpieces. As acoustic sound waves are captured by the resonator, they are directed to the earpieces via the pair of hollow, air-filled tubes.

But acoustic stethoscopes suffer from several drawbacks. For example, an acoustic stethoscope attenuates the acoustic sound waves proportional to the frequency of the source. Thus, the sound conveyed to the earpieces is often very faint, which can make it difficult to accurately diagnose a condition. In fact, due to the variation in sensitivity of the ear, some sounds (e.g., those below 50 hertz (Hz)) may not be heard at all. Some enterprises have begun developing electronic stethoscopes (also referred to as "stethophones") to address the drawbacks of acoustic stethoscopes.

Electronic stethoscopes improve upon acoustic stethoscopes by electronically amplifying sounds heard within a body. For instance, an electronic stethoscope may address the faint sounds originating from within a body under examination by amplifying these sounds. To accomplish this, the electronic stethoscope converts acoustic sound waves received by a microphone placed in the chestpiece into an electrical signal, and then amplifies the electronical signal for optimal listening.

However, amplification may result in undesirable digital artifacts that make it more difficult to diagnose conditions affecting the body. Moreover, component cutoffs (e.g., the frequency response thresholds of microphones, amplifiers, and speakers) may limit electronic stethoscopes' utility by simultaneously amplifying mid-frequency sounds and attenuating high- and low-frequency sounds.

Unlike acoustic stethoscopes, the designs of electronic stethoscopes vary widely. While electronic stethoscopes may include different arrangements of microphones, amplifiers, processors, etc., many electronic stethoscopes include a single downward-facing microphone that is placed within the resonator. But such a design suffers significant interference from ambient noise.

BRIEF DESCRIPTION OF THE DRAWINGS

Various features of the technology will become more apparent to those skilled in the art from a study of the Detailed Description in conjunction with the drawings.

FIG. 10 depicts several examples of microelectron-mechanical systems ("MEMS") microphones.

FIG. 11 depicts a flow diagram of a process for monitoring a biometric characteristic using an electronic stethoscope system having one or more input units and a hub unit.

Figure 1:
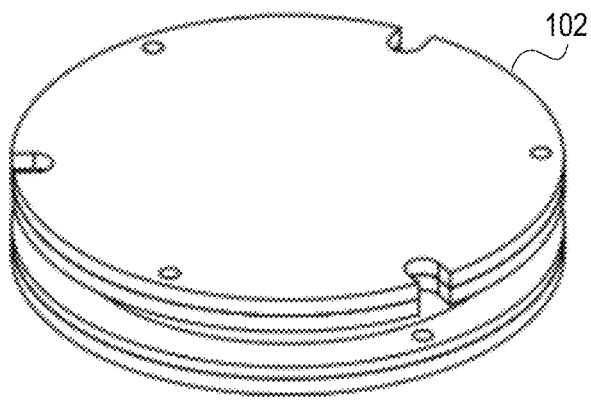
FIG. 1 includes a top perspective view of an input unit for an electronic stethoscope system.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

Introduced here are electronic stethoscope systems designed to simultaneously monitor sounds originating from within a body under examination and the ambient environment. An electronic stethoscope system can include one or more input units (also referred to as "chestpieces") that are connected to a hub unit. Each input unit may have a conical resonator designed to direct acoustic sound waves toward at least one microphone configured to produce audio data indicative of internal sounds. These microphone(s) may be referred to as an "auscultation microphones." Moreover, the input unit may include at least one microphone configured to produce audio data indicative of sounds external to the body under examination. These microphone(s) may be referred to as "ambient microphones" or "environmental microphones." For the purpose of illustration, an "ambient microphone" may be described as capable of producing audio data indicative of "ambient sounds." However, these "ambient sounds" generally a combination of sounds produced by three different sources: (1) sounds originating from within the ambient environment (e.g., environmental noise); (2) sounds leaked through the conical resonator; and (3) sounds that penetrate the body under examination. Examples of ambient sounds include sounds originating directly from the structural body of the input unit (e.g., scratching by the finger or chest) and low-frequency environmental noises that penetrate the structural body of the input unit.

To improve the quality of sound recorded by the input unit, a processor can apply a noise cancellation algorithm that considers as input the audio data produced by the auscultation microphone(s) and the audio data produced by the ambient microphone(s). For example, by examining the audio data produced by the ambient microphone(s), the processor may discover which artifacts, if any, should be filtered from the audio data produced by the auscultation microphone(s). In some embodiments, each input unit includes a processor. Thus, the audio data received by the hub unit from each input unit may be pre-processed. In other embodiments, the hub unit is solely responsible for processing the audio data received from the input unit(s).

Embodiments may be described with reference to particular input unit configurations, networks, etc. However, those skilled in the art will recognize that these features are equally applicable to other input unit configurations, network types, etc. For example, although an electronic stethoscope system may be described as being connected to another computing device via the Internet, the electronic stethoscope system could instead be connected to the other computing device via a Bluetooth communication channel.

Moreover, the technology may be embodied using special-purpose hardware (e.g., circuitry), programmable circuitry appropriately programmed with software and/or firmware, or a combination of special-purpose hardware and programmable circuitry. Accordingly, embodiments of the electronic stethoscope system may include a machine-readable medium having instructions that may be used to program a processor to perform a process for examining audio data indicative of recorded sound waves, parsing the audio data to identify diagnostically relevant features, discovering a pattern for a biometric characteristic (e.g., respiratory rate, heart rate, or degree of wheezing, crackling, etc.), etc.

Terminology

Brief definitions of terms, abbreviations, and phrases used throughout the application are given below.

The terms "connected," "coupled," or any variant thereof means any connection/coupling, either direct or indirect, between two or more elements. The coupling or connection between the elements can be physical and/or logical. For example, two components could be coupled directly to one another or via intermediary channel(s) or component(s).

The term "module" refers broadly to software components, hardware components, and/or firmware components. Modules are typically functional components that can generate useful data or other output(s) based on specified input(s). A module may be self-contained. A computer program may include one or more modules. Thus, a computer program may include multiple modules responsible for completing different tasks or a single module responsible for completing all tasks.

Technology Overview

FIG. 1 includes a top perspective view of an input unit 100 for an electronic stethoscope system. For convenience, the input unit 100 may be referred to as a "stethoscope patch," though, as further described below, the input unit may only include a subset of the components necessary for auscultation. The input unit 100 may also be referred to as a "chestpiece" since it will often be affixed to the chest of a body. However, those skilled in the art will recognize that the input unit 100 may be affixed to other parts of the body as well (e.g., the abdomen or the back).

As further described below, the input unit 100 can collect acoustic sound waves representative of biological activities within a body under examination, convert the acoustic sound waves into an electrical signal, and then digitize the electrical signal (e.g., for easier transmission, to ensure higher fidelity, etc.). The input unit 100 can include a structural body 102 comprised of metal, such as stainless steel, aluminum, titanium, or another suitable metal alloy. To make the structural body 102, molten metal will typically be die casted and then either machined or extruded into the appropriate form.

In some embodiments, the input unit 100 includes a casing that inhibits exposure of the structural body 102 to the ambient environment. For example, the casing may prevent contamination, improve cleanability, etc. Generally, the casing encapsulates substantially all of the structural body 102 except for the conical resonator disposed along its bottom side. The conical resonator is described in greater depth below with respect to FIGS. 3A-B. The casing may be comprised of silicon rubber, polypropylene, polyethylene, or any other suitable material. Moreover, in some embodiments, the casing includes an additive whose presence limits microbial growth, ultraviolet (UV) degradation, etc.

Figure 2A:
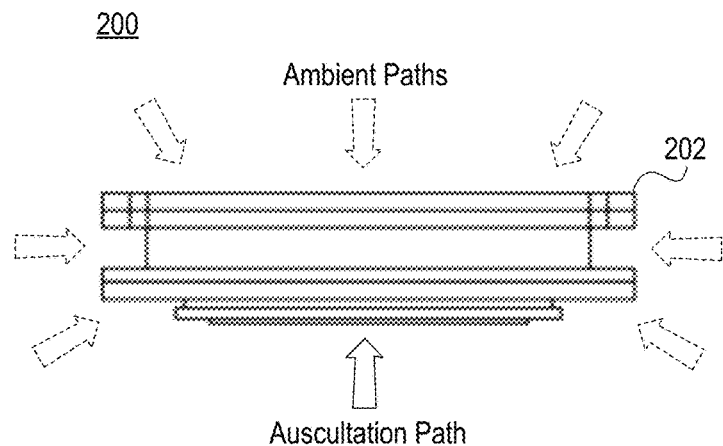
FIG. 2A includes a side view of an input unit for an electronic stethoscope system.
Figure 2B:
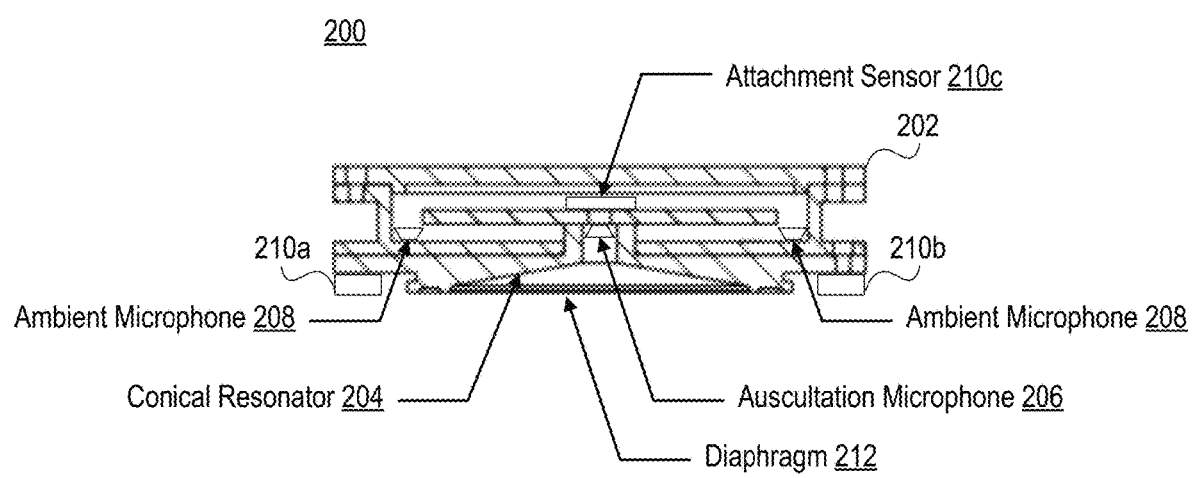
FIG. 2B includes a side cross-sectional view of the input unit.

FIG. 2A includes a side view of an input unit 200 for an electronic stethoscope system, while FIG. 2B includes a side cross-sectional view of the input unit 200. Often, the input unit 200 includes a structural body 202 having an interior cavity defined therein. The structural body 202 of the input unit 200 may have a conical resonator 204 designed to direct acoustic sound waves toward a microphone residing within the interior cavity. In some embodiments, a diaphragm 212 (also referred to as a "vibration film") extends across the wider opening (also referred to as the "outer opening") of the conical resonator 204. The diaphragm 212 can be used to listen to high-pitch sounds, such as those often produced by the lungs. The diaphragm 212 can be formed from a thin plastic disk comprised of an epoxy-fiberglass compound or glass fibers.

To improve the clarity of acoustic sound waves collected by the conical resonator 204, the input unit 200 may be designed to simultaneously monitor sounds originating from different locations. For example, the input unit 200 may be designed to simultaneously monitor sounds originating from within a body under examination and sounds originating from the ambient environment. Thus, the input unit 200 may include at least one microphone 206 (referred to as an "auscultation microphone") configured to produce audio data indicative of internal sounds and at least one microphone 208 (referred to as an "ambient microphone") configured to produce audio data indicative of ambient sounds. Each of the auscultation and ambient microphones includes a transducer able to convert acoustic sound waves into an electrical signal. Thereafter, the electrical signal may be digitized prior to transmission to a hub unit. Digitization enables the hub unit to readily clock/synchronize the signals received from multiple input units. Digitization may also ensure that the signal received by the hub unit from an input unit has a higher fidelity than would otherwise be possible.

These microphones may be omnidirectional microphones designed to pick up sound from all directions or directional microphones designed to pick up sounds coming from a specific direction. For example, the input unit 200 may include auscultation microphone(s) 206 oriented to pick up sounds originating from a space adjacent to the outer opening of the conical resonator 204. In such embodiments, the ambient microphone(s) 208 may be omnidirectional or directional microphones. As another example, a set of ambient microphones 208 could be equally spaced within the structural body 202 of the input unit 200 to form a phased array able to capture highly-directional ambient sounds to reduce noise and interference. Accordingly, the auscultation microphone(s) 206 may be arranged to focus on the path of incoming internal sounds (also referred to as the "auscultation path"), while the ambient microphone(s) 208 may be arranged to focus on the paths of incoming ambient sounds (also referred to as the "ambient paths").

Conventionally, electronic stethoscopes subject electrical signals indicative of acoustic sound waves to digital signal processing (DSP) algorithms responsible for filtering undesirable artifacts. However, such action may suppress nearly all of the sound within certain frequency ranges (e.g., 100-800 Hz), thereby greatly distorting internal sounds of interest (e.g., those corresponding to heartbeats, inhalations, or exhalations). Here, however, a processor can employ a noise cancellation algorithm that separately examines the audio data generated by the auscultation microphone(s) 206 and the audio data generated by the ambient microphone(s) 208. More specifically, the processor may parse the audio data generated by the ambient microphone(s) 208 to determine how, if at all, the audio data generated by the auscultation microphone(s) 206 should be modified. For example, the processor may discover that certain digital features should be amplified (e.g., because they correspond to internal sounds), diminished (e.g., because they correspond to ambient sounds), or removed entirely (e.g., because they represent noise). Such a technique can be used to improve the clarity, detail, and quality of sound recorded by the input unit 200. For example, application of the noise cancellation algorithm may be an integral part of the denoising process employed by an electronic stethoscope system that includes at least one input unit 200.

For privacy purposes, neither the auscultation microphone(s) 206 nor the ambient microphone(s) 208 may be permitted to record while the conical resonator 204 is directed away from the body. Thus, in some embodiments, the auscultation microphone(s) 206 and/or the ambient microphone(s) 208 do not begin recording until the input unit 200 is attached to body. In such embodiments, the input unit 200 may include one or more attachment sensors 210a-c that are responsible for determining whether the structural body 202 has been properly secured to the surface of the body.

The input unit 200 could include any subset of the attachment sensors shown here. For example, in some embodiments, the input unit 200 only includes attachment sensors 210a-b, which are positioned near the wider opening of the conical resonator 204. As another example, in some embodiments, the input unit 200 only includes attachment sensor 210c, which is positioned near the narrower opening (also referred to as the "inner opening") of the conical resonator 204. Moreover, the input unit 200 may include different types of attachment sensors. For example, attachment sensor 210c may be an optical proximity sensor designed to emit light (e.g., infrared light) through the conical resonator 204 and then determine, based on the light reflected back into the conical resonator 204, the distance between the input unit 200 and the surface of the body. As another example, attachment sensors 210a-c may be audio sensors designed to determine, with the assistance of an algorithm programmed to determine the drop-off of a high-frequency signal, whether the structural body 202 is securely sealed against the surface of the body based on the presence of ambient noise (also referred to as "environmental noise").

As another example, attachment sensors 210a-b may be pressure sensors designed to determine whether the structural body 202 is securely sealed against the surface of the body based on the amount of applied pressure. Some embodiments of the input unit 200 include each of these different types of attachment sensors. By considering the output of these attachment sensor(s) 210a-c in combination with the aforementioned active noise cancellation algorithm, a processor may be able to dynamically determine the adhesion state. That is, the processor may be able to determine whether the input unit 200 has formed a seal against the body based on the output of these attachment sensor(s) 210a-c.

Figure 2C:
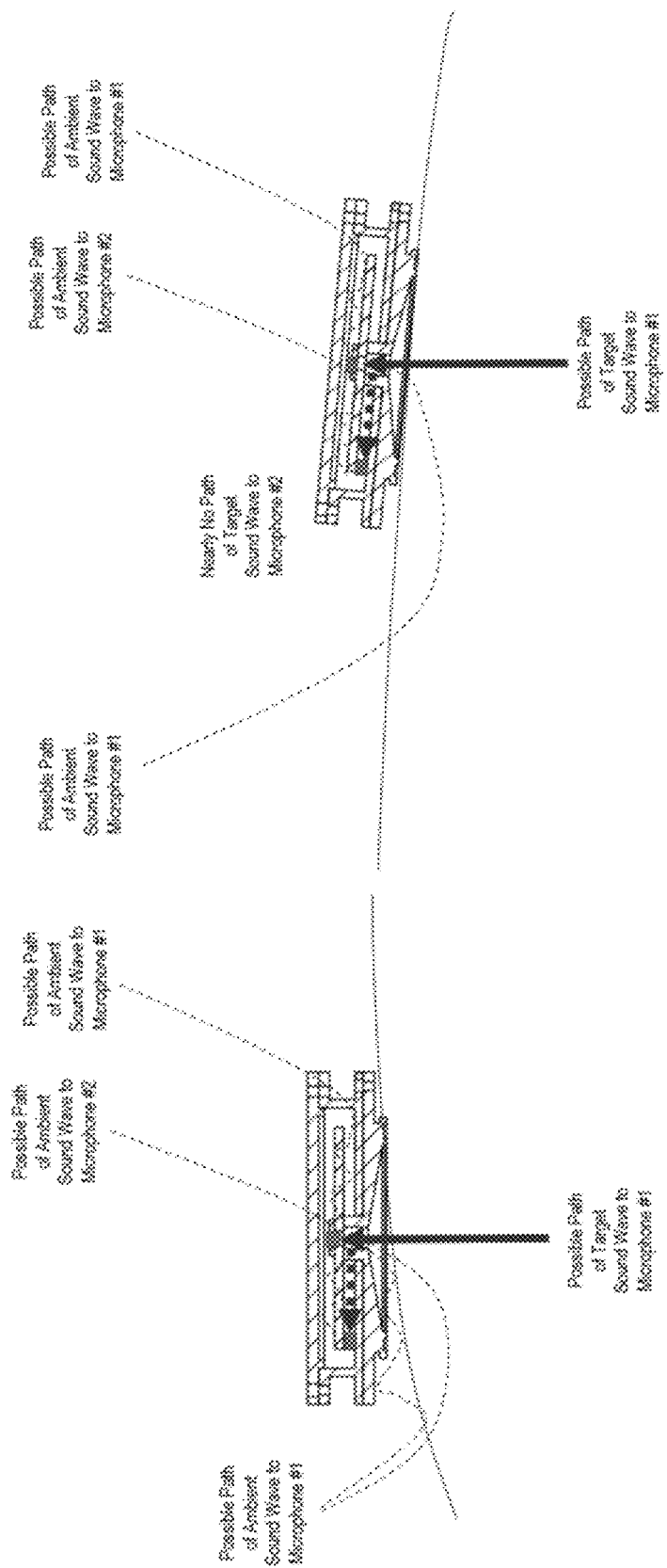
FIG. 2C illustrates the paths of several different sounds that may collectively be referred to as "ambient sounds."

FIG. 2C illustrates the paths of several different sounds that may collectively be referred to as "ambient sounds." Oftentimes, the "ambient sound" recorded by an ambient microphone will actually be a combination of three different sounds: (1) sounds originating from within the ambient environment (e.g., environmental noise); (2) sounds leaked through the conical resonator; and (3) sounds that penetrate the body under examination.

Figure 3A:
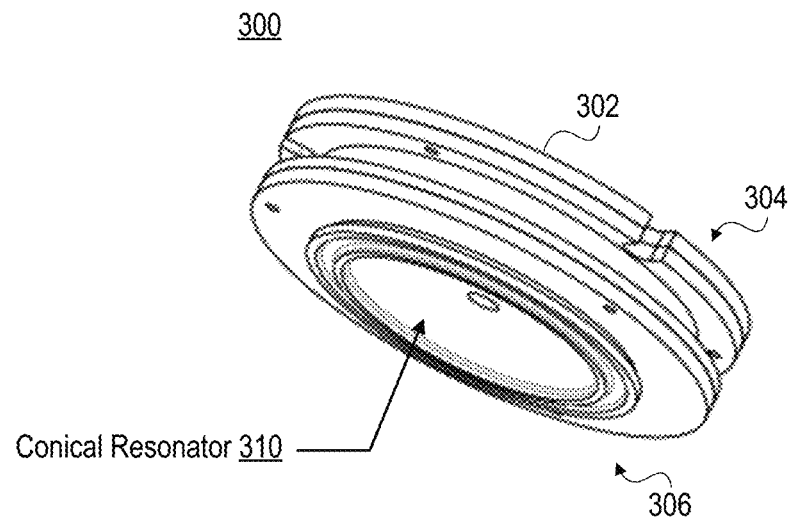
FIGS. 3A-B include bottom perspective views of an input unit for an electronic stethoscope system.
Figure 3B:
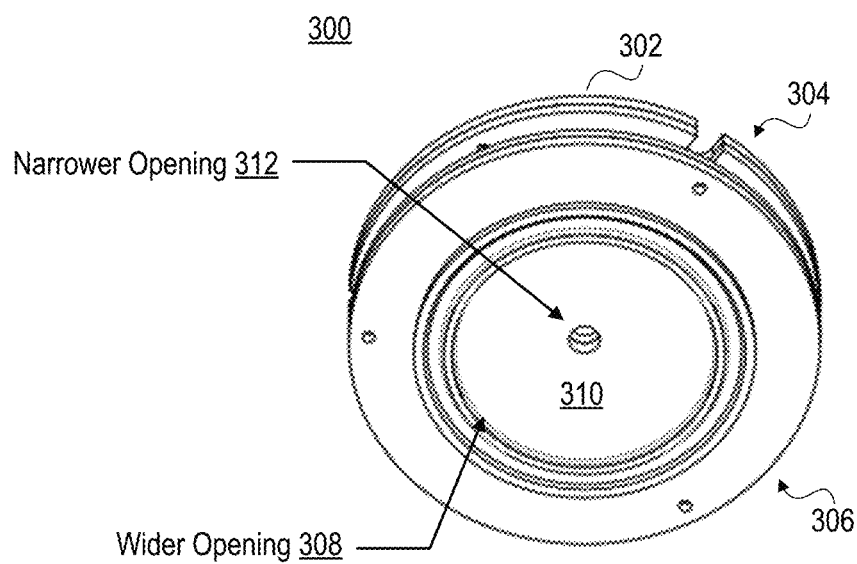

FIGS. 3A-B include bottom perspective views of an input unit 300 for an electronic stethoscope system. As shown here, the input unit 300 includes a structural body 302 having a distal portion 304 and a proximal portion 306. To initiate an auscultation procedure, an individual (e.g., a medical professional, such as a physician or a nurse) can secure the proximal portion 306 of the input unit 300 against the surface of a body under examination. The proximal portion 306 of the input unit 300 can include the wider opening 308 of a conical resonator 310. The conical resonator 310 may be designed to direct acoustic sound waves collected through the wider opening 308 toward a narrower opening 312, which may lead to an auscultation microphone. Conventionally, the wider opening 308 is approximately 30-50 millimeters (mm), 35-45 mm, or 38-40 mm. However, because the input unit 300 described here may have automatic gain control functionality, smaller conical resonators may be used. For example, in some embodiments, the wider opening 308 is less than 30 mm, 20 mm, or 10 mm. Thus, the input units described herein may be able to support a wide variety of conical resonators having different sizes, designed for different applications, etc.

With regard to the terms "distal" and "proximal," unless otherwise specified, the terms refer to the relative positions of the input unit 300 with reference to the body. For example, in referring to an input unit 300 suitable for fixation to the body, "distal" can refer to a first position close to where a cable suitable for conveying digital signals is connected to the input unit 300 and "proximal" can refer to a second position close to where the input unit 300 contacts the body.

Figure 4:
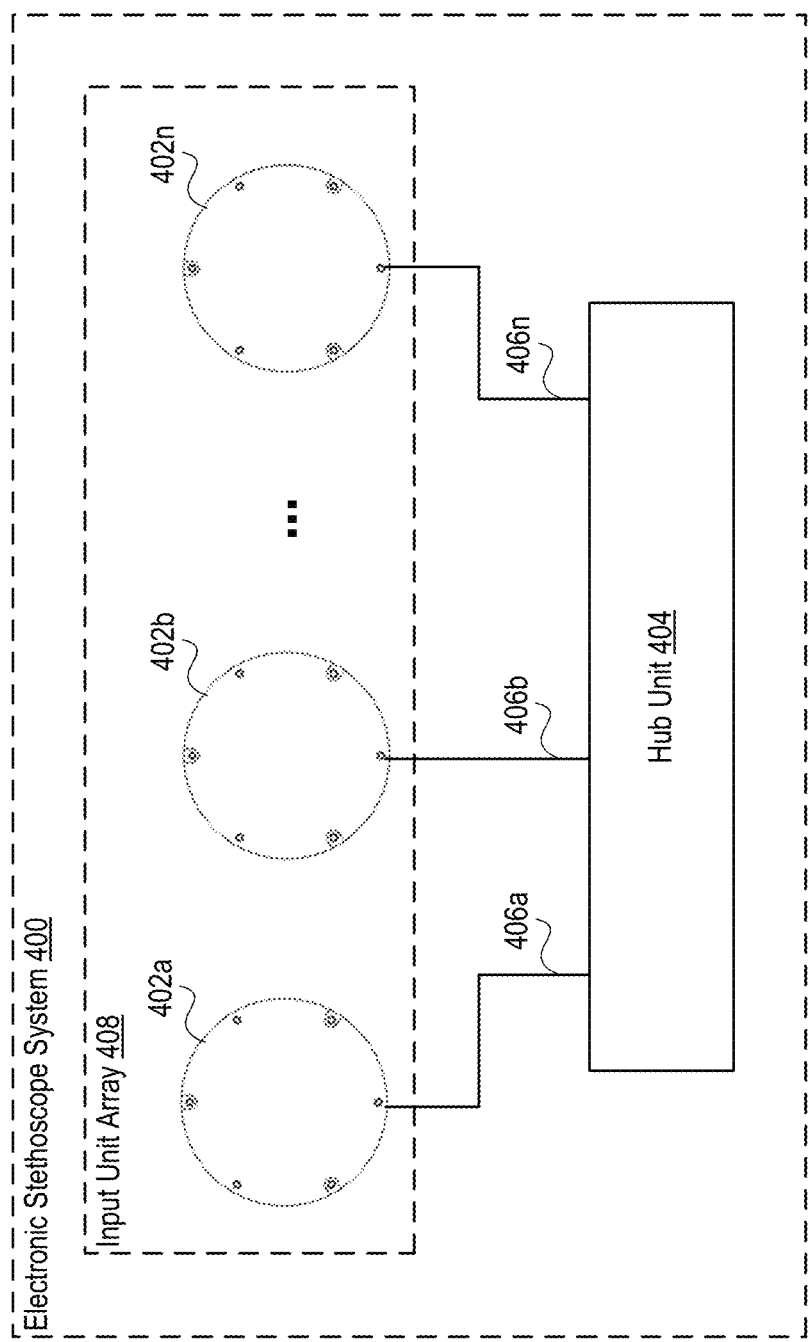
FIG. 4 illustrates how one or more input units can be connected to a hub unit to form an electronic stethoscope system.

FIG. 4 illustrates how one or more input units 402a-n can be connected to a hub unit 404 to form an electronic stethoscope system 400. In some embodiments, multiple input units are connected to the hub unit 404. For example, the electronic stethoscope system 400 may include four input units, six input units, or eight input units. Generally, the electronic stethoscope system 400 will include at least six input units. Electronic stethoscope systems having multiple input units may be referred to as "multi-channel stethoscopes." In other embodiments, only one input unit is connected to the hub unit 404. Electronic stethoscope systems having one input unit may be referred to as "single-channel stethoscopes."

As shown in FIG. 4, each input unit 402a-n can be connected to the hub unit 404 via a corresponding cable 406a-n. Generally, the transmission path formed between each input unit 402a-n and the hub unit 404 via the corresponding cable 406a-n is designed to be substantially free of interference. For example, electronic signals may be digitized by the input units 402a-n prior to transmission to the hub unit 404, and signal fidelity may be ensured by prohibiting the generation/contamination of electromagnetic noise. Examples of cables include ribbon cables, coaxial cables, Universal Serial Bus (USB) cables, High-Definition Multimedia Interface (HDMI) cables, RJ45 ethernet cables, and any other cable suitable for conveying a digital signal. Each cable includes a first end connected to the hub unit 404 (e.g., via a physical port) and a second end connected to the corresponding input unit (e.g., via a physical port). Accordingly, each input unit 402a-n may include a single physical port, and the hub unit 404 may include multiple physical ports. Alternatively, a single cable may be used to connect all of the input units 402a-n to the hub unit 404. In such embodiments, the cable may include a first end capable of interfacing with the hub unit 404 and a series of second ends, each of which is capable of interfacing with a single input unit. Such a cable may be referred to, for example, as a "one-to-two cable," "one-to-four cable," or "one-to-six cable" based on the number of second ends.

When all of the input units 402a-n connected to the hub unit 404 are in an auscultation mode, the electronic stethoscope system 400 can employ an adaptive gain control algorithm programmed to compare internal sounds to ambient sounds. The adaptive gain control algorithm may analyze a target auscultation sound (e.g., normal breathing, wheezing, crackling, etc.) to judge whether an adequate sound level has been achieved. For example, the adaptive gain control algorithm may determine whether the sound level exceeds a predetermined threshold. The adaptive gain control algorithm may be designed to achieve gain control of up to 100 times (e.g., in two different stages). The gain level may be adaptively adjusted based on the number of input units in the input unit array 408, as well as the level of sound recorded by the auscultation microphone(s) in each input unit. In some embodiments, the adaptive gain control algorithm is programmed for deployment as part of a feedback loop. Thus, the adaptive gain control algorithm may apply gain to audio recorded by an input unit, determine whether the audio exceeds a preprogrammed intensity threshold, and dynamically determine whether additional gain is necessary based on the determination.

Because the electronic stethoscope system 400 can deploy the adaptive gain control algorithm during a post-processing procedure, the input unit array 408 may be permitted to collect information regarding a wide range of sounds caused by the heart, lungs, etc. Because the input units 402a-n in the input unit array 408 can be placed in different anatomical positions along the surface of the body (or on an entirely different body), different biometric characteristic (e.g., respiratory rate, heart rate, or degree of wheezing, crackling, etc.) can be simultaneously monitored by the electronic stethoscope system 400.

Figure 5:
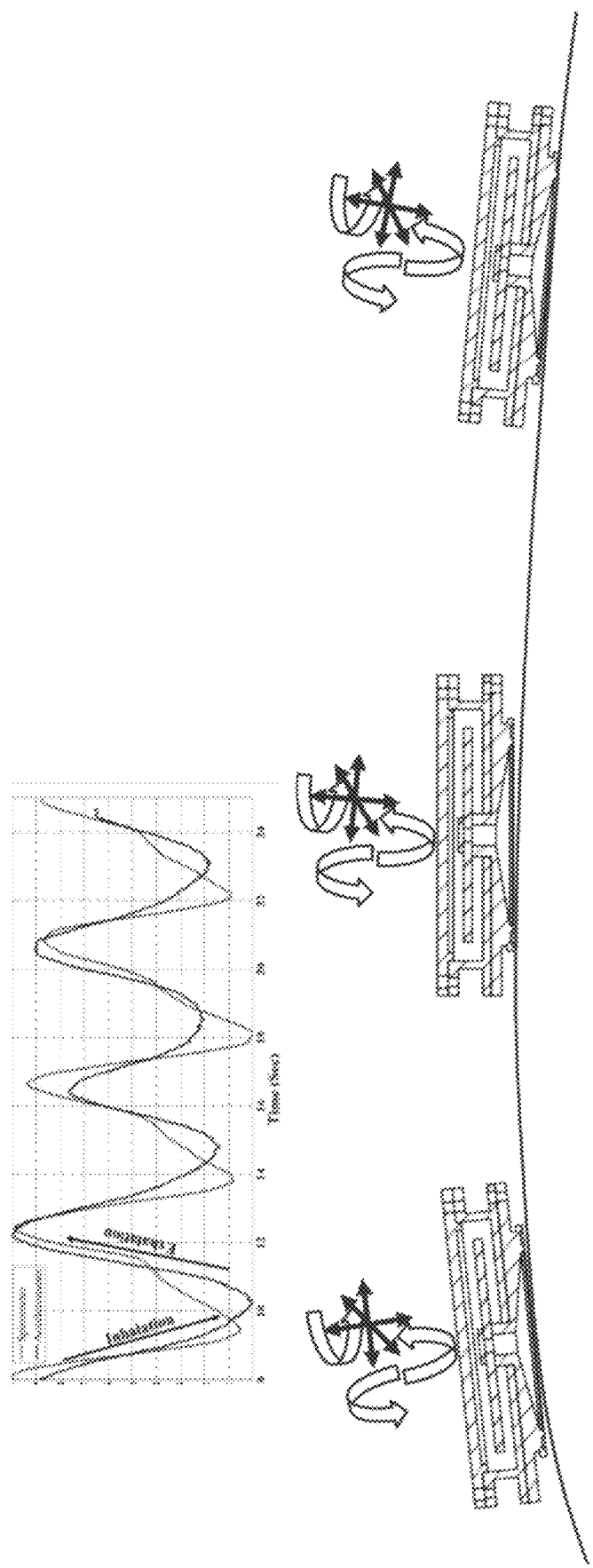
FIG. 5 illustrates how an input unit array can be used to detect the respiratory pattern of a body if each input unit includes an inertial measurement unit (IMU).

FIG. 5 illustrates how an input unit array (e.g., the input unit array 408 of FIG. 4) can be used to detect the respiratory pattern of a body if each input unit includes an inertial measurement unit (IMU). The data generated by an IMU may also be used, for example, to determine the gesture orientation of the body. An IMU is an electronic component designed to measure the force, angular rate, inclination/tilt, and/or magnetic field of an object. Generally, an IMU includes accelerometer(s), gyroscope(s), magnetometer(s), or any combination thereof. Here, for example, each input unit includes a six-axis IMU having a three-axis accelerometer and a three-axis gyroscope.

When each input unit in an input unit array includes an IMU, the electronic stethoscope system can examine the outputs of these IMUs to establish the respiratory pattern of the body on which the input units are affixed. For an individual input unit, a change in acceleration (e.g., as measured by an accelerometer) may be indicative of an inhalation or an exhalation. By synchronizing the outputs of IMUs positioned along different parts of the body, the electronic stethoscope system can establish the respiratory status in conjunction with any internal sounds. For example, the electronic stethoscope system may determine an inhalation is likely to have occurred if the input unit(s) affixed to the upper chest have moved upward while the input unit(s) affixed to the abdomen have remained substantially stationary or moved downward. As another example, the electronic stethoscope system may determine an exhalation is likely to have occurred if the input unit(s) affixed to the upper chest have moved downward while the input unit(s) affixed to the abdomen have remained substantially stationary or moved upward. The electronic stethoscope system may associate internal sounds (e.g., wheezing or crackling) discovered within the audio data with inhalations, exhalations, resting periods, etc. By continually monitoring the respiratory status during an examination, the electronic stethoscope system may be able to better understand the context of the discovered internal sounds.

Figure 6:
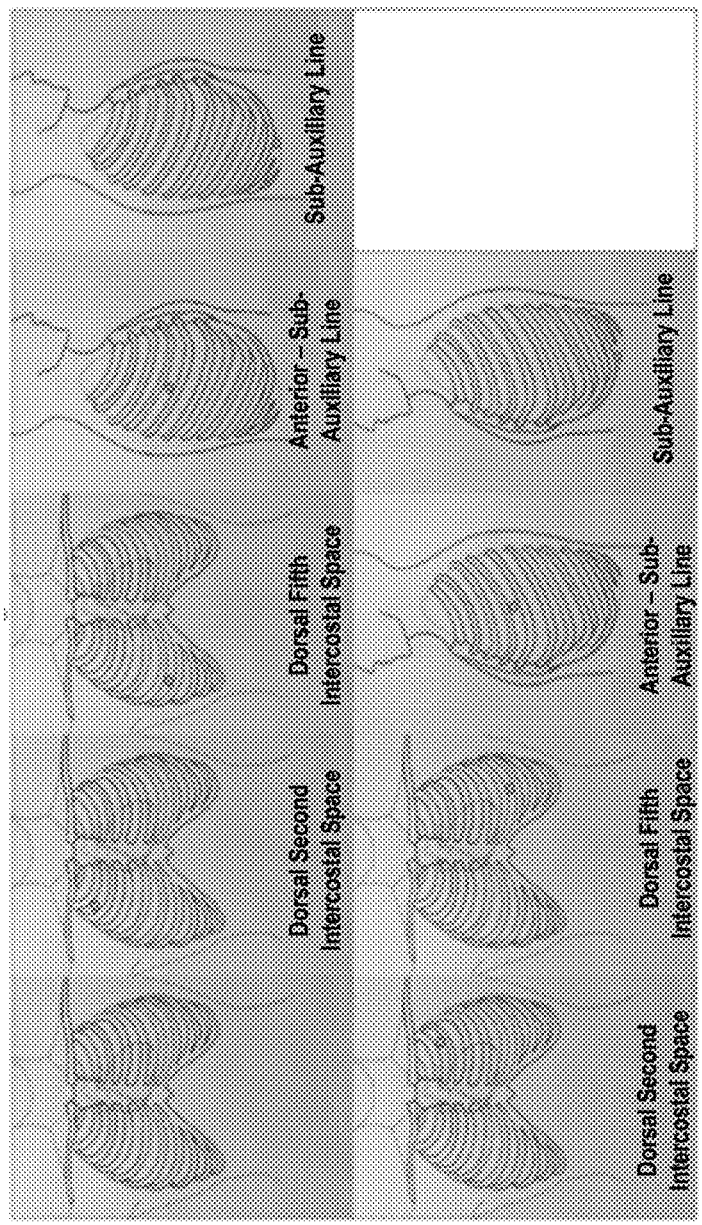
FIG. 6 depicts several different anatomical locations at which an input unit may be positioned.

FIG. 6 depicts several different anatomical locations at which an input unit may be positioned. In a first example, a single input unit is affixed to each of the anatomical locations shown in FIG. 6. For example, an electronic stethoscope system may include four input units arranged along the ventral side of the body, two input units arranged along the left lateral side of the body, and two input units arranged along the right lateral side of the body. Thus, the array may include eight input units capable of simultaneously monitoring internal and ambient sounds. In a second example, a single input unit may be moved amongst these different anatomical locations. By monitoring position/movement of the input unit (e.g., based on data generated by an IMU), a movement path of the input unit can be established. The movement path allows data (e.g., audio data) generated by the input unit to be subsequently mapped to specific anatomical locations. Thus, a single input unit may be moved across the body in such a manner to simulate an array of multiple input units.

Those skilled in the art will recognize that various counts of input units, as well as various arrangements of those input units, may be useful in different situations. Accordingly, depending on which internal sound(s) or organ systems (e.g., the circulatory system, respiratory system, or gastrointestinal system) are of interest, embodiments of an electronic stethoscope system may include different counts of input units, different arrangements of input units, etc.

To facilitate in discovering how the input units in an array have been deployed, each input unit may possess a positional-assisted tracking ability. That is, each input unit may be capable of monitoring its own in three-dimensional geometric space. Moreover, each input unit may be capable of monitoring its own location with respect to other input units in the array (e.g., via Bluetooth beaconing or some other local broadcasting technology). Thus, an electronic stethoscope system may have positional awareness of each input unit (e.g., by monitoring the output of each corresponding IMU), regardless of whether the array includes one input unit or multiple input units.

Positional information may be recorded by a hub unit of the electronic stethoscope system for further review. Such action enables the electronic stethoscope system to track position over time, detect unexpected/expected variations in position, and monitor the unexpected/expected variations. Generally, an "expected variation" is a movement expected to occur during an examination, such as an inhalation or an exhalation. An "unexpected variation," meanwhile, is a movement that is not expected to occur during an examination. Examples of unexpected variations include coughing fits, extended durations without an inhalation or exhalation, etc. In some embodiments, each input unit may be designed to individual establish its own position (e.g., without reference to any other input units).

Accordingly, information regarding the position of each input unit may be logged in a memory, which may be included in the hub unit or in a separate recording system (e.g., a network-accessible storage). Tracking position of the input units over time may also facilitate in labeling the features necessary for semi-supervised machine learning and unsupervised machine learning (e.g., in the context of constructing auscultation models). For instance, a diagnostic platform may discover, by examining audio data in relation to the positional data, which feature(s) to monitor before, during, or after inhalations. Similarly, the diagnostic platform may discover which feature(s) to monitor before, during, or after exhalations. The diagnostic platform may reside on the electronic stethoscope system or another computing device (e.g., a mobile phone or a network-accessible server system) that is communicatively coupled to the electronic stethoscope system.

As noted above, in some embodiments, each input unit may be able to communicate with other nearby input unit(s) for tracking purposes. For example, the input units in an array may communicate with one another (e.g., via Bluetooth beaconing or some other local broadcasting technology) to establish their position with respect to the other input units in the array. Such a feature may be useful during deployment of the input units (e.g., an input unit may indicate when it is in an appropriate location with respect to other input units in the array) or during post-processing (e.g., a hub component may determine how to process multiple sets of audio data based on the locations of the corresponding input units).

Figure 7:
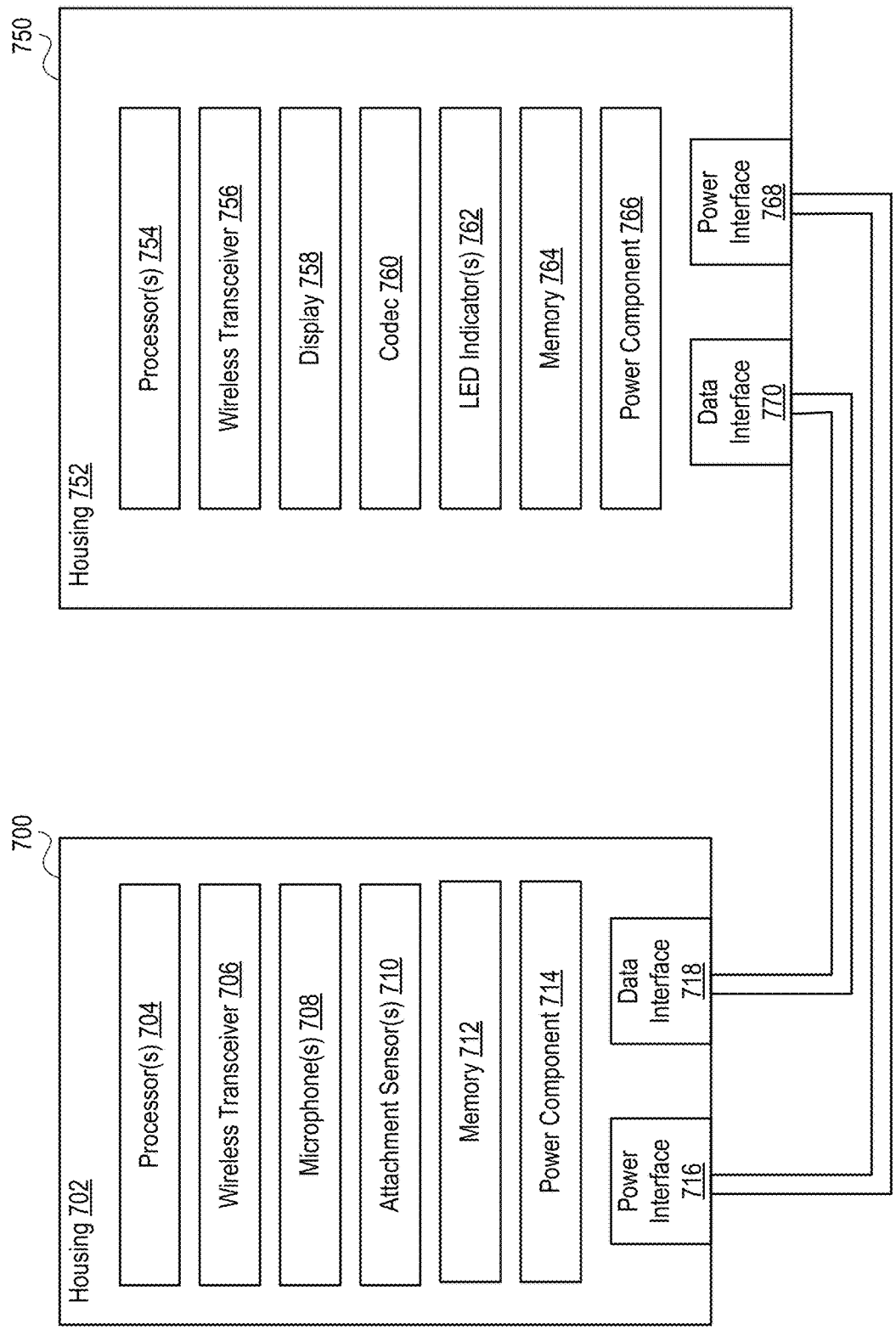
FIG. 7 is a high-level block diagram illustrating exemplary components of an input unit and a hub unit of an electronic stethoscope system.

FIG. 7 is a high-level block diagram illustrating exemplary components of an input unit 700 and a hub unit 750 of an electronic stethoscope system. Embodiments of the input unit 700 and the hub unit 750 can include any subset of the components shown in FIG. 7, as well as additional components not illustrated here. For example, some embodiments of the input unit 700 include a biometric sensor capable of monitoring a biometric characteristic of the body, such as perspiration (e.g., based on skin humidity), temperature, etc. Additionally or alternatively, the biometric sensor may be designed to monitor a breathing pattern (also referred to as a "respiratory pattern"), record electrical activity of the heart, etc.

The input unit 700 can include one or more processors 704, a wireless transceiver 706, one or more microphones 708, one or more attachment sensors 710, a memory 712, and/or a power component 714 electrically coupled to a power interface 716. These components may reside within a housing 702 (also referred to as a "structural body").

As noted above, the microphone(s) 708 can convert acoustic sound waves into an electrical signal. The microphone(s) 708 may include auscultation microphone(s) configured to produce audio data indicative of internal sounds, ambient microphone(s) configured to produce audio data indicative of ambient sounds, or any combination thereof. Audio data representative of values of the electrical signal can be stored, at least temporarily, in the memory 712. In some embodiments, the processor(s) 704 process the audio data prior to transmission downstream to the hub unit 750. For example, the processor(s) 704 may apply algorithms designed for digital signal processing, denoising, gain control, noise cancellation, artifact removal, feature identification, etc. In other embodiments, minimal processing is performed by the processor(s) 704 prior to transmission downstream to the hub unit 750. For example, the processor(s) 704 may simply append metadata to the audio data that specifies the identity of the input unit 700 or examine metadata already added to the audio data by the microphone(s) 708.

In some embodiments, the input unit 700 and the hub unit 750 transmit data between one another via a cable connected between corresponding data interfaces 718, 770. For example, audio data generated by the microphone(s) 708 may be forwarded to the data interface 718 of the input unit 700 for transmission to the data interface 770 of the hub unit 750. Alternatively, the data interface 770 may be part of the wireless transceiver 756. The wireless transceiver 706 could be configured to automatically establish a wireless connection with the wireless transceiver 756 of the hub unit 750. The wireless transceivers 706, 756 may communicate with one another via a bi-directional communication protocol, such as Near Field Communication (NFC), wireless Universal Serial Bus (USB), Bluetooth, Wi-Fi, a cellular data protocol (e.g., LTE, 3G, 4G, or 5G), or a proprietary point-to-point protocol.

The input unit 700 may include a power component 714 able to provide power to the other components residing within the housing 702, as necessary. Similarly, the hub unit 750 can include a power component 766 able to provide power to the other components residing within the housing 752. Examples of power components include rechargeable lithium-ion (Li-Ion) batteries, rechargeable nickel-metal hydride (NiMH) batteries, rechargeable nickel-cadmium (NiCad) batteries, etc. In some embodiments, the input unit 700 does not include a dedicated power component, and thus must receive power from the hub unit 750. A cable designed to facilitate the transmission of power (e.g., via a physical connection of electrical contacts) may be connected between a power interface 716 of the input unit 700 and a power interface 768 of the hub unit 750.

The power channel (i.e., the channel between power interface 716 and power interface 768) and the data channel (i.e., the channel between data interface 718 and data interface 770) have been shown as separate channels for the purpose of illustration only. Those skilled in the art will recognize that these channels could be included in the same cable. Thus, a single cable capable of carrying data and power may be coupled between the input unit 700 and the hub unit 750.

The hub unit 750 can include one or more processors 754, a wireless transceiver 756, a display 758, a codec 760, one or more light-emitting diode (LED) indicators 762, a memory 764, and a power component 766. These components may reside within a housing 752 (also referred to as a "structural body"). As noted above, embodiments of the hub unit 750 may include any subset of these components, as well as additional components not shown here. For example, some embodiments of the hub unit 750 include a display 758 for presenting information such as the respiratory status or the heartrate of an individual under examination, a network connectivity status, a power connectivity status, a connectivity status for the input unit 700, etc. The display 758 may be controlled via tactile input mechanisms (e.g., buttons accessible along the surface of the housing 752), audio input mechanisms (e.g., voice commands), etc. As another example, some embodiments of the hub unit 750 include LED indicator(s) 762 for operation guidance rather than the display 758. In such embodiments, the LED indicator(s) 762 may convey similar information as the display 758 would have. As another example, some embodiments of the hub unit 750 include a display 758 and LED indicator(s) 762.

Upon receiving audio data representative of the electrical signal generated by the microphone(s) 708 of the input unit 700, the hub unit 750 may provide the audio data to a codec 760 responsible for decoding the incoming data. The codec 760 may, for example, decode the audio data (e.g. by reversing encoding applied by the input unit 700) for editing, processing, etc. The codec 760 may be designed to sequentially or simultaneously process audio data generated by the auscultation microphone(s) in the input unit 700 and audio data generated by the ambient microphone(s) in the input unit 700.

Thereafter, the processor(s) 754 can process the audio data. Much like the processor(s) 704 of the input unit 700, the processor(s) 754 of the hub unit 750 may apply algorithms designed for digital signal processing, denoising, gain control, noise cancellation, artifact removal, feature identification, etc. Some of these algorithms may not be necessary if already applied by the processor(s) 704 of the input unit 700. For example, in some embodiments the processor(s) 754 of the hub unit 750 apply algorithm(s) to discover diagnostically relevant features in the audio data, while in other embodiments such action may not be necessary if the processor(s) 704 of the input unit 700 have already discovered the diagnostically relevant features. Generally, a diagnostically relevant feature will correspond to a pattern of values in the audio data matching a predetermined pattern-defining parameter. As another example, in some embodiments the processor(s) 754 of the hub unit 750 apply algorithm(s) to reduce noise in the audio data to improve the signal-to-noise (SNR) ratio, while in other embodiments these algorithm(s) are instead applied by the processor(s) 704 of the input unit 700.

In addition to the power interface 768, the hub unit 750 may include a power port. The power port (also referred to as a "power jack") enables the hub unit 750 to be physically connected to a power source (e.g., an electrical outlet). The power port may be capable of interfacing with different connector types (e.g., C13, C15, C19). Additionally or alternatively, the hub unit may include a power receiver having an integrated circuit ("chip") able to wirelessly receive power from an external source. The power receiver may be configured to receive power transmitted in accordance with the Qi standard developed by the Wireless Power Consortium or some other wireless power standard.

In some embodiments, the housing 752 of the hub unit 750 includes an audio port. The audio port (also referred to as an "audio jack") is a receptacle that can be used to transmit signals, such as audio, to an appropriate plug of an attachment, such as headphones. An audio port typically includes, two, three, or four contacts that enable audio signals to be readily transmitted when an appropriate plug is inserted into the audio port. For example, most headphones include a plug designed for a 3.5-millimeter (mm) audio port. Additionally or alternatively, the wireless transceiver 756 of the hub unit 750 may be able to transmit audio signals directly to wireless headphones (e.g., via NFC, Bluetooth, etc.).

As noted above, the processor(s) 704 of the input unit 700 and/or the processor(s) 754 of the hub unit 750 can apply a variety of algorithms to support different functionalities. Examples of such functionalities include:
Attenuation of lost data packets in the audio data;
Noise-dependent volume control;
Dynamic range compression;
Automatic gain control;
Equalization;
Noise suppression; and
Acoustic echo cancellation.

Each functionality may correspond to a separate module residing in a memory (e.g., memory 712 of the input unit 700 or memory 764 of the hub unit 750). Thus, the input unit 700 and the hub unit 750 may include an attenuation module, a volume control module, a compression module, a gain control module, an equalization module, a noise suppression module, an echo cancellation module, or any combination thereof.

Figure 8:
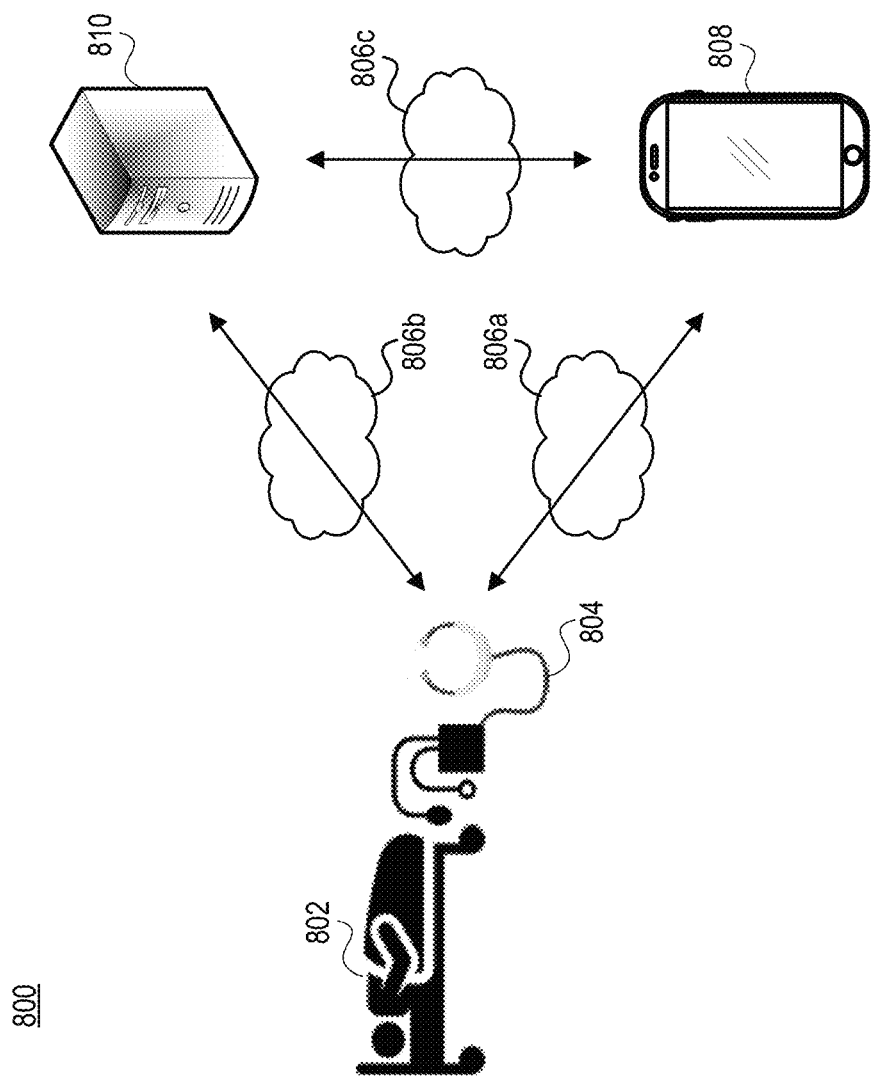
FIG. 8 depicts an example of a network environment that includes an electronic stethoscope system attached to a subject under examination.

FIG. 8 depicts an example of a network environment 800 that includes an electronic stethoscope system 804 attached to a subject 802 under examination. The electronic stethoscope system 804 may be responsible for generating audio data indicative of internal sounds, audio data indicative of ambient sounds, or any combination thereof. Collectively, these different types of audio data may be referred to as "audio data." The electronic stethoscope system 804 can be configured to transmit audio data to one or more computing devices. Here, for example, the electronic stethoscope system 804 transmits audio data to a mobile phone 808 and a network-accessible server system 810 (collectively referred to as the "networked devices").

The networked devices can be connected to the electronic stethoscope system 804 (and to each other) via one or more networks 806a-c. The network(s) 806a-c can include personal area networks (PANs), local area networks (LANs), wide area networks (WANs), metropolitan area networks (MANs), cellular networks, the Internet, etc. Additionally or alternatively, the networked devices may communicate with the electronic stethoscope system 804 (or one another) over a short-range communication protocol. For example, the electronic stethoscope system 804 may transmit audio data to a mobile phone 808 (e.g., via a Bluetooth communication channel), and then the mobile phone 808 may transmit at least some of the audio data to the network-accessible server system 810 (e.g., via a Wi-Fi communication channel or a cellular communication channel). As another example, the electronic stethoscope system 804 may transmit audio data directly to the network-accessible server system 810 (e.g., via a Wi-Fi communication channel or a cellular communication channel).

A diagnostic platform configured to process audio data, parse the audio data to identify diagnostically relevant features, discover a pattern for a biometric characteristic (e.g., respiratory rate or heart rate), or render diagnoses may reside on any of the networked devices. For example, the diagnostic platform may reside on the mobile phone 808, the network-accessible server system 810, or any combination thereof.

Individuals (e.g., subjects or medical professionals, such as physicians and nurses) can interface with the diagnostic platform via an interface. The interface is preferably accessible via a web browser, desktop application, mobile application, or over-the-top (OTT) application. Accordingly, the interface may be viewed on the mobile phone 808, a personal computer, tablet computer, personal digital assistant (PDA), game console, music player, wearable electronic device (e.g., a watch or fitness accessory), network-connected ("smart") electronic device, (e.g., a television or home assistant device), virtual/augmented reality system (e.g., a head-mounted display), or some other electronic device.

In some embodiments, the electronic stethoscope system 804 transmits audio data to the networked devices in real time. For example, the electronic stethoscope system 804 may continually upload audio data to a networked device so long as it remains communicatively coupled to the networked device. Therefore, an individual may observe the audio data (or analyses of such data) on the interface while the electronic stethoscope system 804 is deployed. In other embodiments, the electronic stethoscope system 804 transmits audio data (or analyses of such data) to a networked device on a periodic basis (e.g., hourly, daily, or weekly).

Figure 9:
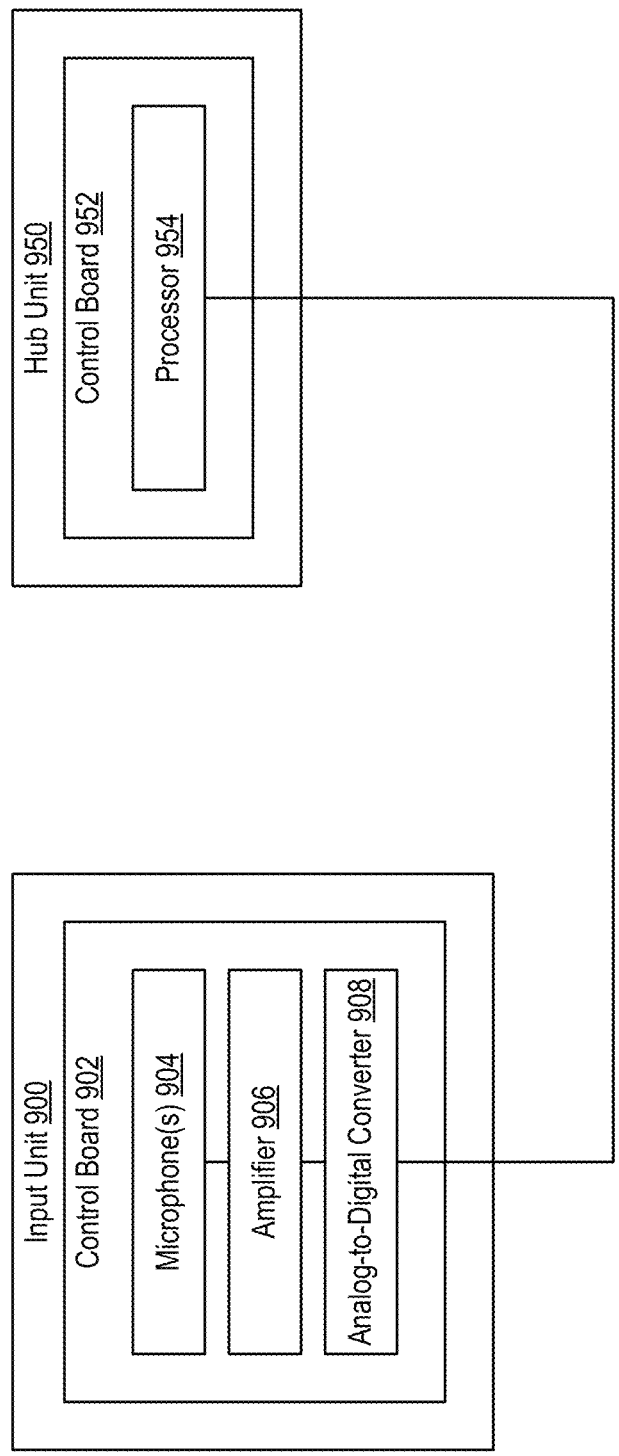
FIG. 9 includes a generalized illustration of how audio data generated by an input unit may be processed prior to transmission to a hub unit.

FIG. 9 includes a generalized illustration of how audio data generated by an input unit 900 may be processed prior to transmission to a hub unit 950. As shown here, the input unit 900 may include one or more microphones 904, an amplifier 906, and an analog-digital converter 908 that are electrically connected to a control board 902 (also referred to as a "printed circuit board" or "circuit board").

Initially, the microphone(s) 904 can generate audio data indicative of internal sounds originating from within a body under examination and/or ambient sounds originating from the ambient environment. The microphone(s) 904 may include microelectron-mechanical systems ("MEMS") microphones whose output leverages high-performance MEMS elements. Several examples of MEMS microphones are shown in FIG. 10. MEMS microphones produce an output voltage that is proportional to the instantaneous air pressure level. MEMS microphones usually have three pins: the output; the power supply voltage (e.g., $V_{DD}$); and ground. In comparison to conventional microphones, MEMS microphones offer higher SNR, lower power consumption, and better sensitivity.

Audio data generated by the microphone(s) 904 may be provided to an amplifier 906 designed to automatically apply gain in a controlled manner to improve the audio data (e.g., by increasing SNR). Thereafter, an analog-to-digital converter 908 can convert the audio data into a digital signal. That is, the analog-to-digital converter 908 may convert the continuous-time, continuous-amplitude analog signal representative of the audio data into a discrete-time, discrete-amplitude digital signal. While conversion introduces a small amount of noise (e.g., due to quantization of the analog input), the digital output ensures that electromagnetic interference (EMI) is largely avoided. Moreover, conversion may ensure that data received by the hub unit 950 from multiple input units is in a compatible format. The digital output may be synchronous across all input unit(s) connected to the hub unit 950.

The hub unit 950, meanwhile, can include a processor 954 that is electrically connected to a control board 952. Initially, the processor 954 can aggregate the digital signal(s) received from the input unit(s) connected to the hub unit 950. The hub unit 950 may be connected to 1, 2, 4, 6, 8, 12, or 16 input units. Moreover, the processor 954 may synchronously process these digital signal(s). In some embodiments, the hub unit 950 includes a microphone that generates audio data indicative of ambient sounds originating from the ambient environment. In such embodiments, the processor 954 may concurrently perform a noise cancellation process for each digital signal based on the audio data recorded by the microphone.

FIG. 11 depicts a flow diagram of a process 1100 for monitoring a biometric characteristic using an electronic stethoscope system having one or more input units and a hub unit. Initially, the electronic stethoscope system determines whether the input unit(s) have been properly secured to the surface of a body under examination (step 1101). For example, a processor may examine data generated by the attachment sensor(s) of each input unit to establish an adhesion status for each input unit. Examples of attachment sensors include optical proximity sensors, audio sensors, pressure sensors, etc. In some embodiments, the electronic stethoscope system is configured to perform such analysis automatically (e.g., without requiring input from an individual).

In response to determining that the input unit(s) have been properly secured to the surface of the body, the electronic stethoscope system can generate audio data by initiating recording by microphone(s) housed within each input unit (step 1102). The microphone(s) may include auscultation microphone(s) configured to produce audio data indicative of internal sounds, ambient microphone(s) configured to produce audio data indicative of ambient sounds, or any combination thereof. In some embodiments, the audio data generated by each input unit is stored, at least temporarily, in a memory housed within the corresponding input unit.

Thereafter, each input unit can transmit its audio data to a hub unit for further review (step 1103). In some embodiments, each input unit process the audio data prior to transmission downstream to the hub unit. For example, an input unit may apply algorithms designed for digital signal processing, denoising, gain control, noise cancellation, artifact removal, feature identification, etc. In other embodiments, minimal processing is performed by the input units prior to transmission downstream to the hub unit. For example, the input unit may simply append metadata to the audio data that specifies the source or examine metadata already added to the audio data (e.g., by the microphone(s) responsible for generating it).

Following receipt of the audio data from the input unit(s), the hub unit can discover or monitor a biometric characteristic by examining the audio data (step 1104). Examples of biometric characteristics include respiratory rate, heart rate, degree of wheezing/crackling, etc. To discover the biometric characteristic, the hub unit may apply algorithm(s) designed to identify segments of audio data having values that roughly match a predetermined pattern-defining parameter. Similarly, to monitor the biometric characteristic, the hub unit may apply algorithm(s) designed to establish the variation between consecutive occurrences of a biological event (e.g., an inhalation or an exhalation), the variation between biological events (e.g., heartbeats) experienced by the body and those in a target sample, etc. For example, the hub unit may compare heartbeats to a series of target samples in order to discover whether any abnormalities are present.

In some embodiments, the hub unit causes display of information related to the biometric characteristic (step 1105). For example, information regarding the biometric characteristic may be presented on a display for review by an individual (e.g., a medical professional, such as a physician or a nurse). Additionally or alternatively, the information may be displayed on another computing device. For example, the hub unit may transmit audio data (or analyses of such data) to another computing device for further review. Similarly, the hub unit may transmit at least some of the audio data (or analyses of such data) to another computing device across a network (step 1106). Examples of computing devices include mobile phones, tablet computers, wearable electronic devices, and network-accessible server systems.

Unless contrary to physical possibility, it is envisioned that the steps described above may be performed in various sequences and combinations. For example, the hub unit may be configured to stream the audio data to another computing device in real time (e.g., before actually examining the audio data itself). Other steps may also be included in some embodiments. For example, each input unit may be configured to process the audio data prior to transmitting it to the hub unit for further review.

Processing System

Figure 12:
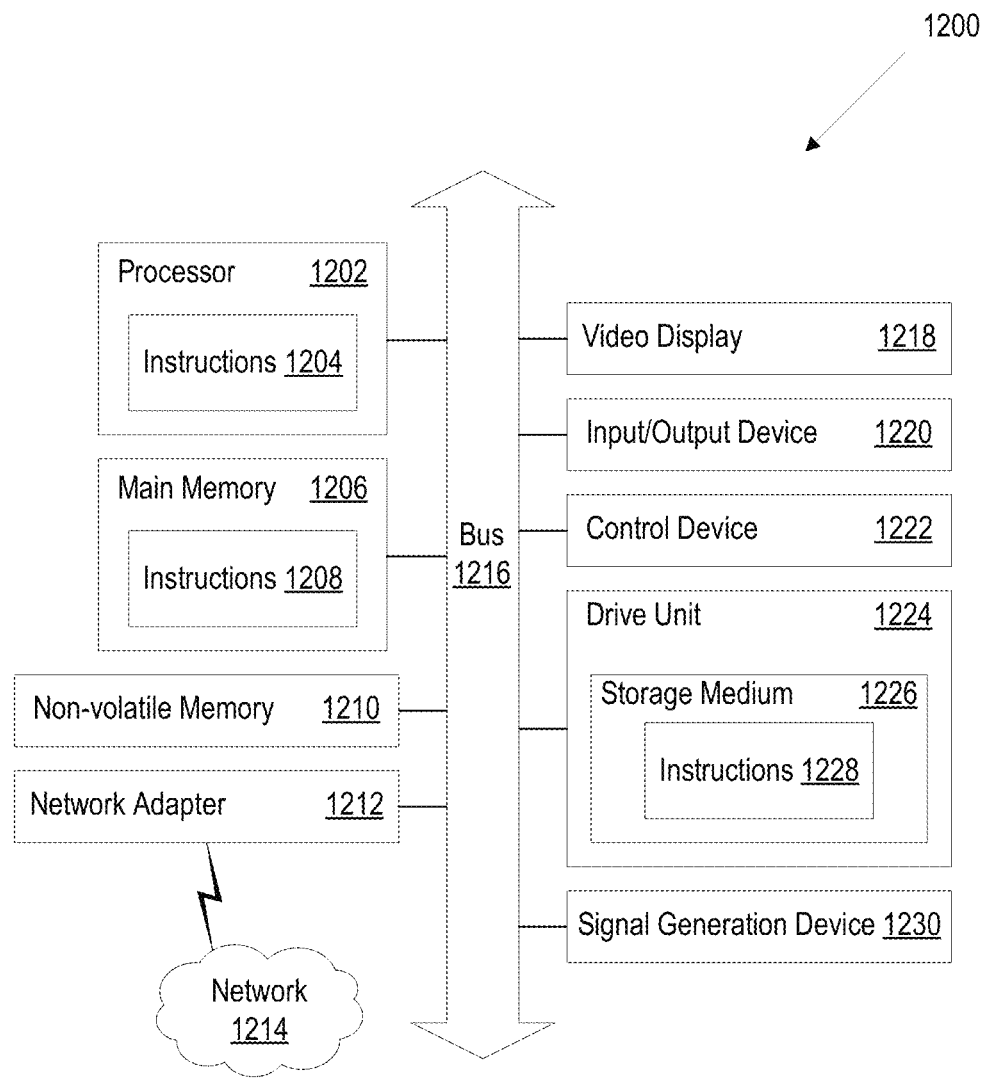
FIG. 12 is a block diagram illustrating an example of a processing system in which at least some operations described herein can be implemented.

FIG. 12 is a block diagram illustrating an example of a processing system 1200 in which at least some operations described herein can be implemented. For example, some components of the processing system 1200 may be hosted entirely on an input unit (e.g., input unit 700 of FIG. 7), entirely on a hub unit (e.g., hub unit 750 of FIG. 7), or distributed amongst a hub unit and its input unit(s). As another example, some components of the processing system 1200 may be hosted on a computing device that is communicatively coupled to a hub unit of an electronic stethoscope system.

The processing system 1200 may include one or more central processing units ("processors") 1202, main memory 1206, non-volatile memory 1210, network adapter 1212 (e.g., network interface), video display 1218, input/output devices 1220, control device 1222 (e.g., keyboard and pointing devices), drive unit 1224 including a storage medium 1226, and signal generation device 1230 that are communicatively connected to a bus 1216. The bus 1216 is illustrated as an abstraction that represents one or more physical buses and/or point-to-point connections that are connected by appropriate bridges, adapters, or controllers. The bus 1216, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 1200 may share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the processing system 1200.

While the main memory 1206, non-volatile memory 1210, and storage medium 1226 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 1228. The term "machine-readable medium" and "storage medium" shall also be taken to include any medium that is capable of storing, encoding, or carrying a set of instructions for execution by the processing system 1200.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1204, 1208, 1228) set at various times in various memory and storage devices in a computing device. When read and executed by the one or more processors 1202, the instruction(s) cause the processing system 1200 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 1210, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 1212 enables the processing system 1200 to mediate data in a network 1214 with an entity that is external to the processing system 1200 through any communication protocol supported by the processing system 1200 and the external entity. The network adapter 1212 can include a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 1212 may include a firewall that governs and/or manages permission to access/proxy data in a computer network, and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

Remarks

The foregoing description of various embodiments of the technology has been provided for the purposes of illustration and description. It is not intended to be exhaustive or to limit the claimed subject matter to the precise forms disclosed.

Many modifications and variation will be apparent to those skilled in the art. Embodiments were chosen and described in order to best describe the principles of the technology and its practical applications, thereby enabling others skilled in the relevant art to understand the claimed subject matter, the various embodiments, and the various modifications that are suited to the particular uses contemplated.

What is claimed is:

1. An electronic stethoscope system comprising:
an input unit that comprises—
a structural body in which a conical resonator designed to collect acoustic waves corresponding to sounds internal to a living body resides,
an auscultation microphone configured to produce first audio data indicative of the sounds internal to the living body,
an ambient microphone configured to produce second audio data indicative of sounds external to the living body,
a processor configured to append metadata that identifies the input unit to the first and second audio data, and
a data interface to which the first and second audio data are forwarded by the processor for transmission to a hub unit;
the hub unit that comprises—
a data interface at which the first and second audio data are received from the input unit, and
a processor configured to
parse the second audio data to discover an environmental noise external to the living body,
alter the first audio data to mitigate an effect of the environmental noise, and
examine the altered first audio data to detect a biometric characteristic of the living body; and
a cable connected between the data interface of the input unit and the data interface of the hub unit.

2. The electronic stethoscope system of claim 1, wherein the input unit further comprises:
a biometric sensor configured to monitor humidity, temperature, respiratory pattern, electrical activity of the heart, or any combination thereof.

3. The electronic stethoscope system of claim 1, wherein the hub unit further comprises:
a transceiver configured to
effect a bi-directional exchange of information with a computing device via a wireless communication channel, and
transmit the altered first audio data to the computing device in real time via the wireless communication channel so that an individual may review the altered first audio data or analyses of the altered first audio data as an examination occurs.

4. A method for monitoring a biometric characteristic of a living body, the method comprising employing the electronic stethoscope system of claim 1 to perform steps of:
establishing an adhesion status of the input unit based on data generated by an attachment sensor included in the input unit;
determining, based on the adhesion status, that the input unit has been properly secured to a surface of the living body under examination;
in response to said determining,
causing the auscultation microphone to generate the first audio data indicative of the sounds internal to the living body; and
causing the ambient microphone to generate the second audio data indicative of the sounds external to the living body;
initiating a transfer of the first and second audio data from the input unit to the hub unit via the cable; and
examining the first and second audio data to detect a biometric characteristic of the living body.

5. An input unit for an electronic stethoscope system, the input unit comprising:
an auscultation microphone configured to produce first audio data indicative of sounds internal to a living body;
an ambient microphone configured to produce second audio data indicative of sounds external to the living body;
an attachment sensor configured to produce attachment data indicative of an adhesion status of the input unit;
a data interface to which one end of a cable is connected; and
a processor configured to forward the first and second audio data to the data interface for transmission to a hub unit responsible for examining the first and second audio data.

6. The input unit of claim 5, further comprising:
a structural body in which the auscultation microphone, the ambient microphone, the attachment sensor, and the processor reside;
a conical resonator through which acoustic waves corresponding to the sounds internal to the living body that are collected through an outer opening are directed toward the auscultation microphone; and
a diaphragm that extends across the outer opening of the conical resonator.

7. The input unit of claim 6, wherein the auscultation microphone is oriented toward an inner opening of the conical resonator.

8. The input unit of claim 6, wherein the outer opening of the conical resonator is less than 20 millimeters (mm).

9. The input unit of claim 5, wherein the attachment sensor is an audio sensor designed to determine a distance between the input unit and the living body based on acoustic characterization.

10. The input unit of claim 5, wherein the processor is further configured to:
determine, based on the attachment data, whether the input unit is properly adhered to the living body,
in response to a determination that the input unit is properly adhered to the living body,
initiate recording by the auscultation and ambient microphones; and
in response to a determination that the input unit is not properly adhered to the living body,
prevent the auscultation and ambient microphones from recording.

11. The input unit of claim 5, wherein the processor is further configured to:
append metadata that identifies the input unit to the first and second audio data.

12. An input unit for an electronic stethoscope system, the input unit comprising:
an auscultation microphone configured to produce first audio data indicative of sounds internal to a living body;
an ambient microphone configured to produce second audio data indicative of sounds external to the living body;
an inertial measurement unit configured to produce movement data indicative of a force, an inclination, an angular rate, or a magnetic field experienced by the input unit;
a data interface to which one end of a cable is connected; and a processor configured to forward (i) the first audio data, (ii) the second audio data, and (iii) the movement data to the data interface for transmission to a hub unit so as to enable the hub unit to synchronize the input unit with at least one other input unit attached to the living body.

13. An electronic stethoscope system comprising:
an input unit that comprises—
- a first microphone configured to produce first audio data indicative of sounds internal to a living body,
- a second microphone configured to produce second audio data indicative of sounds external to the living body,
- an inertial measurement unit configured to produce movement data indicative of a force, an inclination, an angular rate, or a magnetic field experienced by the input unit, and
- a data interface to which the first audio data, the second audio data, and the movement data are forwarded for transmission to a hub unit;

the hub unit that comprises—
- a data interface at which the first audio data, the second audio data, and the movement data are received form the input unit,
- a processor configured to
  - parse the second audio data to discover an environmental noise external to the living body,
  - alter the first audio data to mitigate an effect of the environmental noise, and
  - synchronize the input unit with at least one other input unit attached to the living body based on the movement data, and
- a transceiver configured to transmit the altered first audio data to a computing device via a wireless communication channel; and a cable connected between the data interface of the input unit and the data interface of the hub unit.

14. The electronic stethoscope system of claim 13, wherein the wireless communication channel is established in accordance with a Bluetooth protocol.

15. The electronic stethoscope system of claim 13, wherein the first microphone, the second microphone, or both are microelectron-mechanical systems (MEMS) microphones.

16. The electronic stethoscope system of claim 13, wherein the input unit further comprises a structural body with a conical resonator designed to direct acoustic waves corresponding to the sounds internal to the living body toward the first microphone.

17. A hub unit for an electronic stethoscope system, the hub unit comprising:
- a data interface through which (i) first audio data indicative of sounds internal to a living body and (ii) second audio data indicative of sounds external to the living body are received from an input unit via a wired communication channel,
  - wherein the first and second audio data have metadata appended thereto that identifies the input unit;
- a processor configured to—
  - parse the second audio data to discover an environmental noise external to the living body, and
  - alter the first audio data to mitigate an effect of the environmental noise; and
- a transceiver configured to transmit the altered first audio data to a computing device via a wireless communication channel.

18. The hub unit of claim 17, wherein the processor is further configured to examine the altered first audio data to detect a biometric characteristic of the living body.

* * * * *